(12) United States Patent
Barden et al.

(10) Patent No.: US 11,170,876 B2
(45) Date of Patent: *Nov. 9, 2021

(54) SYSTEM TO DYNAMICALLY COLLECT AND SYNCHRONIZE DATA WITH MOBILE DEVICES

(71) Applicant: MEI Research, Ltd., Edina, MN (US)

(72) Inventors: Charles Barden, Waconia, MN (US); Jon K. Moon, Edina, MN (US); Jared D. Sieling, Maple Grove, MN (US)

(73) Assignee: MEI Research, Ltd., Edina, MN (US)

( * ) Notice: Subject to any disclaimer, the term of this patent is extended or adjusted under 35 U.S.C. 154(b) by 1068 days.

This patent is subject to a terminal disclaimer.

(21) Appl. No.: 15/602,412

(22) Filed: May 23, 2017

(65) Prior Publication Data

US 2017/0323082 A1 Nov. 9, 2017

Related U.S. Application Data

(63) Continuation of application No. 14/047,614, filed on Oct. 7, 2013, now abandoned, which is a continuation of application No. 13/269,611, filed on Oct. 9, 2011, now Pat. No. 8,554,802.

(60) Provisional application No. 61/391,591, filed on Oct. 9, 2010.

(51) Int. Cl.
*G06F 16/20* (2019.01)
*G16H 10/20* (2018.01)
*G16H 10/60* (2018.01)

(52) U.S. Cl.
CPC ............. *G16H 10/20* (2018.01); *G16H 10/60* (2018.01)

(58) Field of Classification Search
CPC .............. G06F 16/986; G06F 19/3475; G06F 19/3481; G06F 16/24578; G06F 16/9535; G06F 16/2379; G16H 10/20; G16H 10/60
See application file for complete search history.

(56) References Cited

U.S. PATENT DOCUMENTS

| | | |
|---|---|---|
| 5,960,411 A | 9/1999 | Hartman et al. |
| 7,791,495 B1 | 9/2010 | Green et al. |
| 8,054,180 B1 * | 11/2011 | Scofield ................. G06Q 30/06 340/539.13 |
| 8,200,628 B2 | 6/2012 | An et al. |
| 8,554,802 B1 | 10/2013 | Barden et al. |
| 2004/0128183 A1 * | 7/2004 | Challey .................. G06Q 30/02 705/7.32 |

(Continued)

OTHER PUBLICATIONS

"U.S. Appl. No. 13/269,611, Non Final Office Action dated Nov. 23, 2012", 26 pgs.

(Continued)

*Primary Examiner* — Tarek Chbouki
(74) *Attorney, Agent, or Firm* — Schwegman Lundberg & Woessner, P.A.

(57) ABSTRACT

The invention enables bi-directional mobile communication by researchers, clinicians or counselors with their patients and study participants. An exemplary application is ecological momentary assessment of psychological and physical status related to weight management. The system may be combined with objective information to trigger a communication and enhance responses assessed on food choices, dietary intake, physical activity, exertion, mood and companions.

19 Claims, 8 Drawing Sheets

(56) References Cited

U.S. PATENT DOCUMENTS

| | | | |
|---|---|---|---|
| 2005/0010544 A1* | 1/2005 | Sleat | G16H 10/20 706/46 |
| 2005/0154996 A1* | 7/2005 | Othmer | H04L 67/28 715/774 |
| 2006/0075420 A1* | 4/2006 | Ludvig | H04H 60/32 725/9 |
| 2006/0107195 A1* | 5/2006 | Ramaswamy | H04N 21/435 715/203 |
| 2007/0101139 A1* | 5/2007 | Bayer | G06F 21/10 713/168 |
| 2007/0288488 A1 | 12/2007 | Rohrs et al. | |
| 2008/0036784 A1* | 2/2008 | Behar | G06Q 10/10 345/589 |
| 2008/0119131 A1 | 5/2008 | Rao et al. | |
| 2008/0256020 A1 | 10/2008 | Wakefield | |
| 2008/0272541 A1* | 11/2008 | Walker | G07F 17/3267 273/139 |
| 2008/0313010 A1 | 12/2008 | Jepson et al. | |
| 2009/0171616 A1 | 7/2009 | Zhang et al. | |
| 2009/0254851 A1* | 10/2009 | Scott | G06Q 30/02 715/772 |
| 2010/0004975 A1 | 1/2010 | White et al. | |
| 2010/0005055 A1 | 1/2010 | An et al. | |
| 2010/0076785 A1* | 3/2010 | Mehta | G16H 50/20 705/3 |
| 2010/0077095 A1* | 3/2010 | Wong | H04N 21/812 709/231 |
| 2010/0246322 A1 | 9/2010 | Welker | |
| 2010/0250538 A1 | 9/2010 | Richards et al. | |
| 2011/0071003 A1 | 3/2011 | Watterson et al. | |
| 2011/0119130 A1* | 5/2011 | Agan | G06Q 30/02 705/14.49 |
| 2011/0219315 A1 | 9/2011 | Bier et al. | |
| 2012/0066373 A1 | 3/2012 | Ochoa et al. | |
| 2014/0039916 A1 | 2/2014 | Barden et al. | |
| 2014/0046729 A1* | 2/2014 | Meyer | G06Q 10/00 705/7.32 |

OTHER PUBLICATIONS

"U.S. Appl. No. 13/269,611, Notice of Allowance dated Jun. 5, 2013", 18 pgs.

"U.S. Appl. No. 13/269,611, Response filed Feb. 18, 2013 to Non Final Office Action dated Nov. 23, 2012", 11 pgs.

"U.S. Appl. No. 14/047,014, Decision on Pre-Appeal Brief Request dated Aug. 14, 2015", 2 pgs.

"U.S. Appl. No. 14/047,614, Advisory Action dated Mar. 29, 2016", 4 pgs.

"U.S. Appl. No. 14/047,614, Advisory Action dated Apr. 10, 2017", 3 pgs.

"U.S. Appl. No. 14/047,614, Advisory Action dated Jun. 24, 2015", 3 pgs.

"U.S. Appl. No. 14/047,614, Examiner Interview Summary dated Oct. 1, 2015", 3 pgs.

"U.S. Appl. No. 14/047,614, Final Office Action dated Jan. 13, 2017", 16 pgs.

"U.S. Appl. No. 14/047,614, Final Office Action dated Apr. 23, 2015", 14 pgs.

"U.S. Appl. No. 14/047,614, Final Office Action dated Dec. 31, 2015", 15 pgs.

"U.S. Appl. No. 14/047,614, Non Final Office Action dated Jun. 29, 2016", 16 pgs.

"U.S. Appl. No. 14/047,614, Non Final Office Action dated Sep. 1, 2015", 13 pgs.

"U.S. Appl. No. 14/047,614, Non Final Office Action dated Nov. 18, 2014", 15 pgs.

"U.S. Appl. No. 14/047,614, Pre-Appeal Brief Request filed Jul. 21, 2015", 5 pgs.

"U.S. Appl. No. 14/047,614, Preliminary Amendment filed Oct. 9, 2013", 8 pgs.

"U.S. Appl. No. 14/047,614, Response filed Feb. 29, 2016 to Final Office Action dated Dec. 31, 2015", 10 pgs.

"U.S. Appl. No. 14/047,614, Response filed Mar. 13, 2017 to Final Office Action dated Jan. 13, 2017", 8 pgs.

"U.S. Appl. No. 14/047,614, Response filed Jun. 9, 2015 to Final Office Action dated Apr. 23, 2015", 5 pgs.

"U.S. Appl. No. 14/047,614, Response filed Sep. 29, 2016 to Non Final Office Action dated Jun. 29, 2016", 9 pgs.

"U.S. Appl. No. 14/047,614, Response filed Oct. 21, 2015 to Final Office Action dated Sep. 1, 2015", 8 pgs "U.S. Appl. No. 14/047,614, Supplemental Preliminary Amendment filed Apr. 22, 2016", 3 pgs.

"U.S. Appl. No. 14/404,614, Response filed Jan. 20, 2015 to Non Final Office Action dated Nov. 18, 2014", 9 pgs.

* cited by examiner

Manage Triggers

| ID | Annunciation Type | | Trigger | | Trigger Options |
|---|---|---|---|---|---|
| Record Dinner | ○ | Vibrate | ● | Time of Day | Set Time |
| | ○ | Ring | ○ | Activity | 3:00 PM |
| | ○ | Pop Up Box | ○ | Location | |
| Record Activity | ○ | Vibrate | ○ | Time of Day | Select Activity |
| | ● | Text Msg | ● | Activity | Walking |
| | ○ | Pop Up Box | | | Swimming |
| | | | | | Running |
| Entering McDonalds | ○ | Vibrate | ○ | Time of Day | Select Location |
| | ● | Ring/Tone | ○ | Activity | Message |
| | ○ | Text Msg | ● | Location | Should you be Eating at McDonalds? |

Dynamic Survey
Add Question

401 — [input box]

Question type

402 — ○ Text
○ Multiple Choice
○ Single Choice
○ Date/Time

403 — | Add option | Remove option |
404 — [ ]

405 — How many meals did you have? | Delete | Options |
406 — Who did you have dinner with? | Delete | Options |

407 — [Colors]    [Fonts] — 408

○ Blue      ○ Large
○ Gray      ○ Small

[Submit] ———— 409

Figure 4

SYSTEM TO DYNAMICALLY COLLECT AND SYNCHRONIZE DATA WITH MOBILE DEVICES

CROSS-REFERENCE TO RELATED PATENT DOCUMENT

This application is a continuation of U.S. application Ser. No. 14/047,614, filed Oct. 7, 2013, which claims priority to U.S. application Ser. No. 13/269,611, filed Oct. 9, 2011, which claims the benefit of priority to U.S. Provisional Application No. 61/391,591, filed Oct. 9, 2010, each of which are incorporated herein by reference in their entirety.

FIELD OF THE INVENTION

This invention relates to software, communications and methods to assess energy balance; obtain context information on actions and environment; and support individuals, their clinicians or other practitioners to promote a healthy lifestyle by managing weight, diet, addiction and other behaviors. More specifically, the invention can be used to collect information and responses on food choices and intake, activity diaries, ratings of exertion, mood, companions and other input sought by researchers, clinicians, advisers or counselors.

BACKGROUND OF THE INVENTION

The weight status of Americans has been declared a serious public health problem and is already burdening our health care systems. Obesity and low physical activity are prime risks for multiple forms of morbidity and mortality including several chronic diseases (coronary heart disease, Type II Diabetes, arthritis, sleep apnea and some forms of cancer). Obesity and overweight are a result of energy imbalance—excess macronutrient intake and low levels of physical activity.

Unfortunately, past approaches to weight loss treatments have proven ineffective for both children and adults, despite increasing awareness and individual efforts to lose weight. Traditionally effective treatments for overweight individuals need to be intensive enough to cause a change in lifestyle. Techniques to deliver such treatments would overwhelm our healthcare system. Programs also need to reach people with limited finances and who live in locations remote from experienced professionals and clinics. Further, feedback and other support for patients must be adapted to their daily lives and as concurrently as possible with behavior that should be altered.

An exemplary use of the invention is ecological momentary assessment (EMA). EMA is a timely record of actions and environment that preserves immediate psychological and physical status. EMA replaces recall diaries to overcome bias and errors from delayed records. Simple examples of EMA might have a study participant provide a rating of perceived exertion (RPE) after an exercise session or assign a score from a Likert scale to their present mood.

Electronic EMA (eEMA) methods are a further improvement that replace paper surveys and increase privacy. EMA has become a popular tool to collect data and influence behavior change. EMA allows researchers and clinicians to obtain behavioral, social context, and individual cognition in near real time. eEMA has been demonstrated as superior to other methods, especially paper, for avoiding recall bias.

Rofey, et al ["Utilizing Ecological Momentary Assessment in pediatric obesity to quantify behavior, emotion, and sleep", Obesity 18(6): 1270-1272, 2010] stated that, " . . . technological devices that gather objective data have reasonably high compliance rates, and may inform measurement of treatment outcomes in adolescents who are obese". Mobile devices, especially "smartphones" can enhance eEMA with objective measures made by sensors such as time, location, speed, acceleration, temperature, light level, and proximity to locations of interest or electronic devices (including other smartphones) carried by people with a relation to a participant. These additional objective measures can be attached to a particular instance of eEMA (such as a Survey) to provide context. Or, the sensor measurements can be made continuously and the eEMA coordinated with the concurrent record.

There are indications that interventions for weight management, addictive and other deleterious behaviors can provide sustained effectiveness. Multiple factors and behaviors need to be targeted together with timely, personally tailored interventions supported by actionable information. The interventions need to be maintained outside of clinic or group settings and respond to the changing needs of participants. Individualized interventions on multiple behaviors are most important with individuals who are refractory managing their weight (US Dept of Health and Human Services reports). With their rich User Interface and increasingly capable processors smartphones are able to not only gather eEMA information enhanced with objective context they can also bring immediately useful information back to participants in studies or clinical treatments.

The invention could be used in any situation in which a person or entity wishes to collect data from and on individuals who have agreed to provide that data. For example, this invention could be used by market researchers wishing to collect data from potential users of a new product.

OBJECTS OF THE INVENTION

This invention allows a Researcher, to:
create and modify Surveys and Items for individual Participants or groups of Participants;
create Prompts and Annunciations that can be independent or associated with the Surveys;
associate the Annunciations and presentation of the Items with Triggers related to predetermined conditions;
deploy the Surveys to Participant Devices;
present the Surveys to the Participants on demand or in response to Triggers and gather Participant Responses;
gather, organize and attach context to Prompts and Participant Responses;
return the Participant Responses to a remote Server or database;
organize and store the Participant Responses and present them to the Researcher and/or Participant or to predetermined algorithms for automated actions.

BRIEF DESCRIPTION OF THE DRAWINGS

FIG. 3 is an example of a web page to create annunciations, triggers or prompts.

FIG. 4 is an example of a web designer form to create Survey questions.

GLOSSARY

Figure 1:
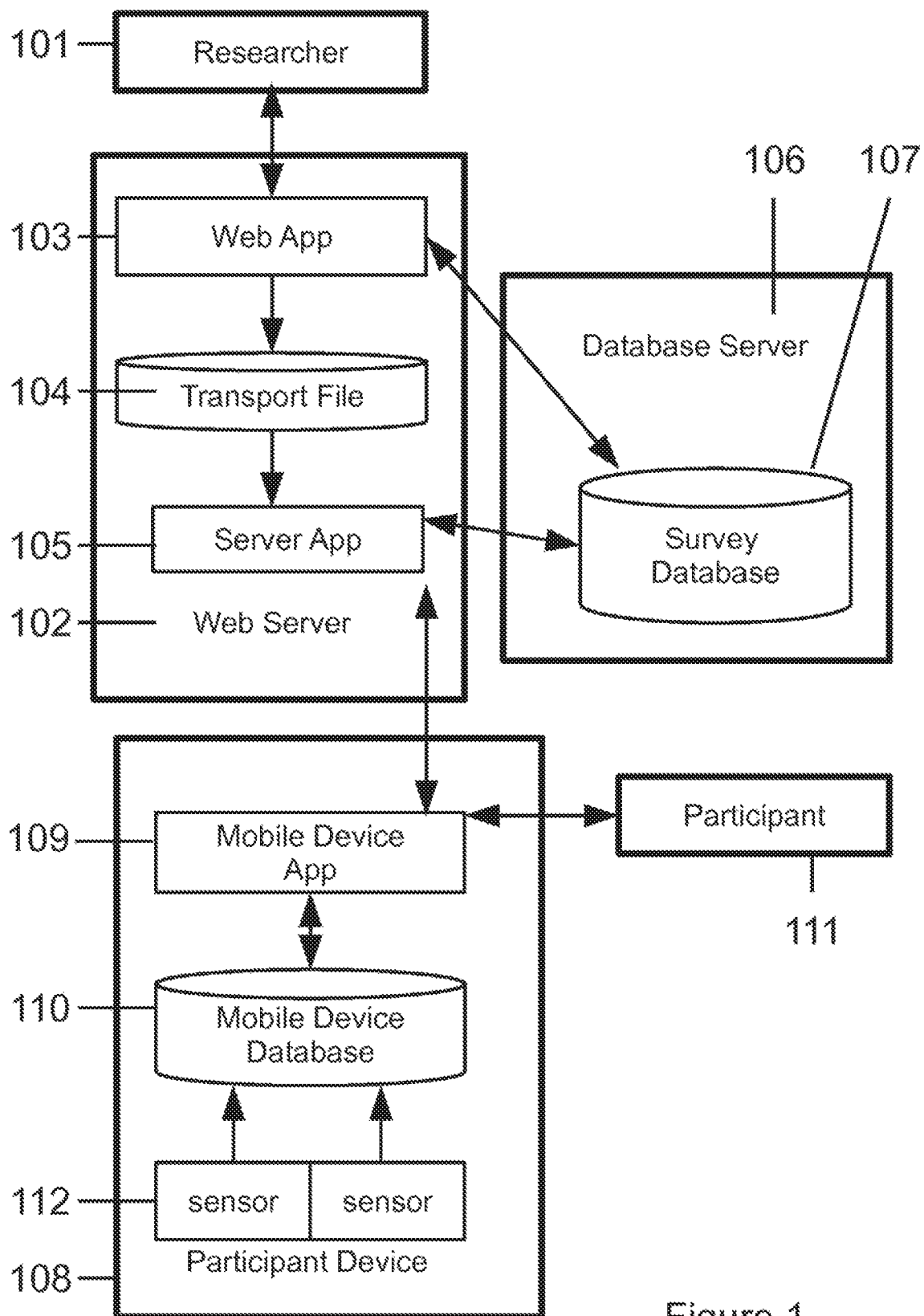
FIG. 1 is a block diagram of the system components and flow of information.
Figure 2:
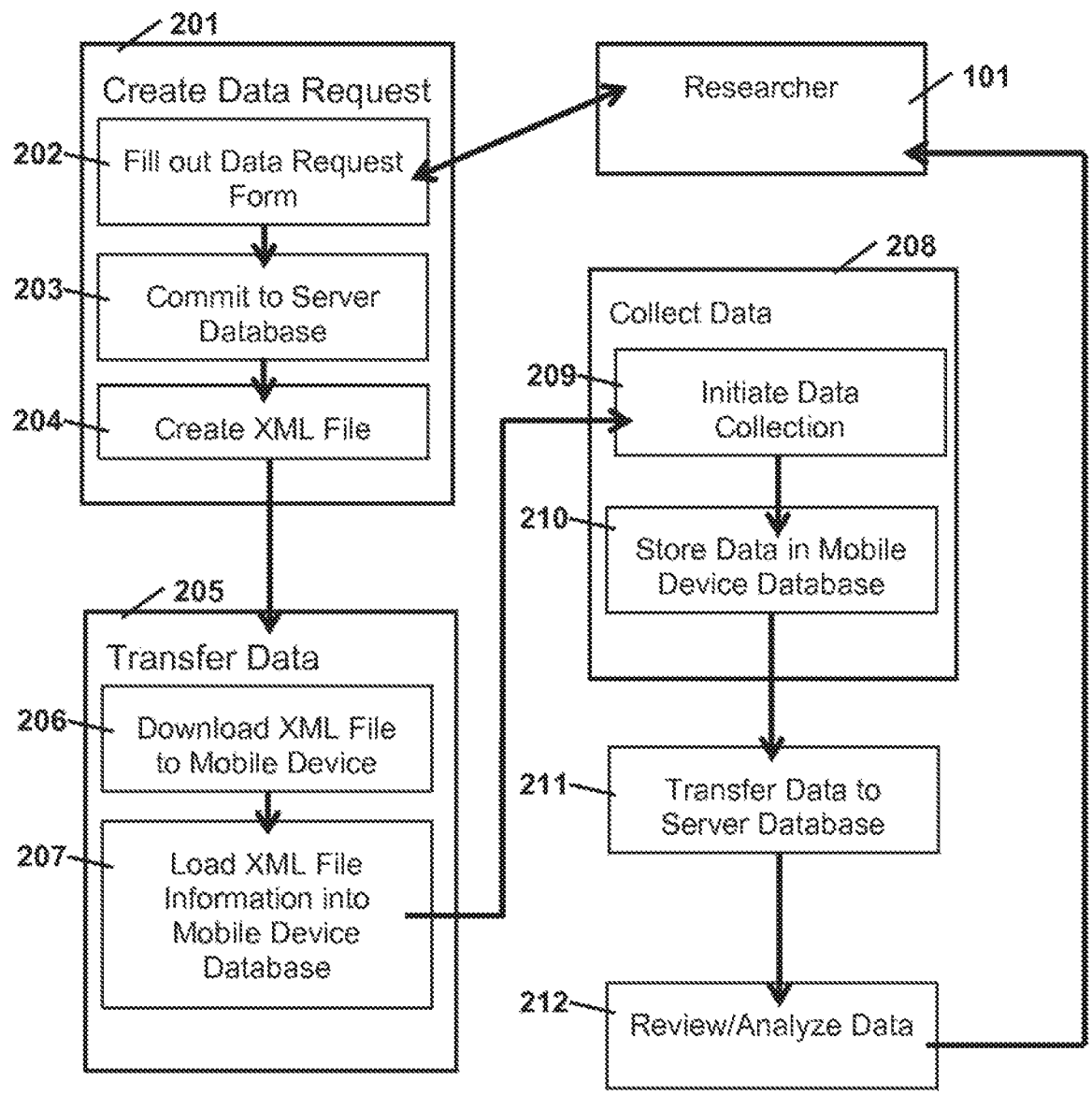
FIG. 2 is a flow diagram showing the steps in the process to create and deploy a Data Request to a Participant Device; collect, store and upload data to a central Server Database; and extract, view and analyze the collected data.

Researcher—an investigator, clinician, other person or entity desiring to collect information from or interact with one or more Participants.

Participant—a patient or other person, often enrolled in a research study, with whom a Researcher wishes to interact to provide and gather information.

Participant Device—computing device, typically having a display with touch or keyboard input, such as a personal computer or mobile device (e.g., smartphone or personal digital assistant).

App or Application—software program automatically performing singular or multiple related tasks.

Server—a computer, or assemblage of computers, that link other computers or electronic devices together, providing services across a network such as the internet.

Web Server—a computer program running on a server that delivers (serves) and receives content over the internet.

Database Server—a computer program that provides database services to other computing devices, such as personal computers or Participant Devices.

Data Request—request for data from an application operating on a device separate from the device receiving the request.

Survey—a data request or other assemblage of one or more Items to be presented according to metadata and other characteristics on a Participant Device Item—a Prompt, and associated answers if the Prompt is in the form of a question, presented to a Participant as part of a Survey User Interface—a part of an Application that controls a display for a Researcher or the Participant that allows the Researcher or Participant to interact with the system Metadata—data that provides context or additional information about other data and/or its means of presentation.

php script—a web-based Application that is executed by a Web Server

XML—extensible markup language is a set of rules for encoding documents electronically Transport file—a structured file, such as XML or Json, containing one or more Surveys to facilitate download to a Participant device.

Download—the transfer of a Transport file or other data from a Server to a Participant device Upload—the transfer of Survey information and other data from a Participant device to a Server PDA—personal digital assistant Compile—the process of creating an Application from source code Json—javascript object notation is a format for encoding data or code electronically AJAX—asynchronous javascript with XML is a method to create client based interactive web applications Buddy Box—a radio transponder to notify a Participant Device it is at a specific location.

Geolocation—absolute position obtained from GPS (a satellite-based navigation system consisting of a network of orbiting satellites), radio-frequency communication with cellular towers or other means Proximity—location or distance relative to a geolocation, person or object.

Ping—a computer network administration utility used to test the reachability of a host on an Internet Protocol (IP) network and to measure the round-trip time for messages sent from the originating host to a destination computer Annunciation—a sound, vibration, light or other means of notifying a participant of a prompt.

Trigger—one or more pre-determined conditions that cause a Survey to be presented on a Participant Device.

Prompt—information presented to a participant, including but not limited to, a statement, recommendation, command or question.

Participant Response—information provided by a Participant through a Participant Device.

Context Data—data that describes the content of the data including but not limited to time and location.

DETAILED DESCRIPTION OF THE INVENTION

System Overview

The present invention is a system to allow a Researcher (101) to easily and dynamically manage the collection and synchronization of data of various types from one or more Participants (111) via a Participant Device (108), then to process, validate and review the returned data. For case of understanding, examples in this description employ terminology from Javascript® for Android® on participant devices and on operations on a server use SQLite® and php script. One skilled in the art will be familiar with essentially equivalent operations and terminology used on other systems.

FIG. 1 is a block diagram of one implementation of such a system. In FIG. 1 the boxes are elements of the system and arrows indicate information flow between elements.

Figure 5:
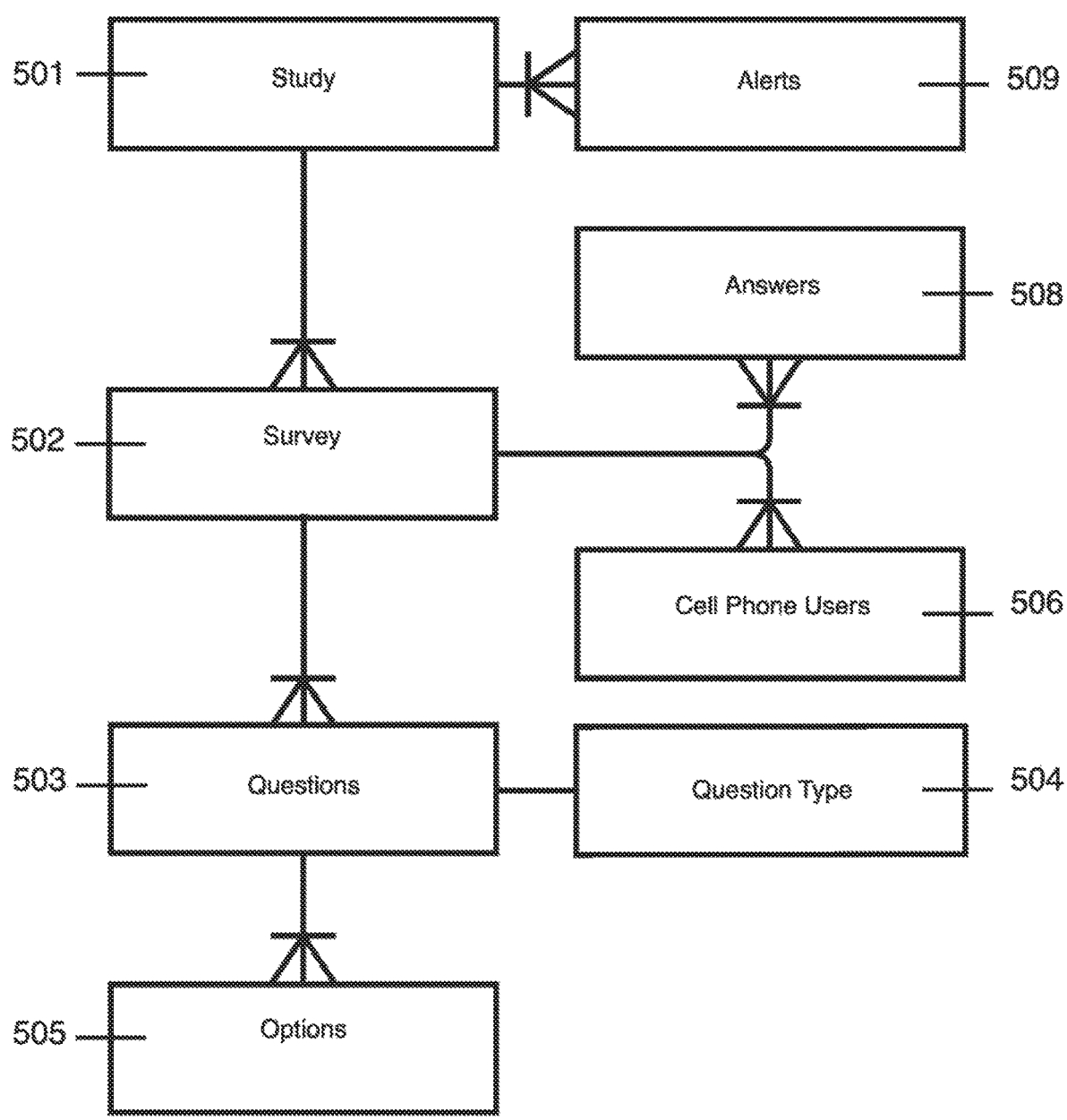
FIG. 5 is an entity relationship diagram of the Server Database tables and their relationship to each other.

The Server Database (107) is a relational database such as provided by MySQL or Oracle. It stores data about the Participants and the study being conducted by the Researcher, Metadata about the data to be collected, and the data collected. In our implementation, the data is stored in tables that are in $3^{rd}$ normal form and data integrity is enforced with foreign keys. An example of tables and structure for the Server Database is shown in FIG. 5. This example is for a study using Smartphones as the Participant Devices and collecting only Participant Response data. The Server Database will be customized, expanded or contracted for each study, depending on the data to be collected. Examples of data that could be collected include physical or physiologic sensor signals, Participant Responses, images, GPS data and audio notes or voice annotations by the Participant. The tables in FIG. 5 are:

Study (501)—master table holding the organization and Researchers responsible for studies.

Survey (502)—a child of the Study table dedicated to a unique study.

Questions (503)—a child of the Survey table that holds unique questions for a study.

QuestionType (504)—a table holding available types of questions that enforces referential integrity to the Question table.

Options (505)—a child of the Question table that holds multiple options choices for questions.

CellPhoneUsers (506)—a table that holds the unique ID, such as a Participant Device IMEI, that is tied to the Survey table via a foreign key.

Answers (508)—a table that holds all the answers that Participants answered on their Participant Device and uploaded to the remote Server Alerts (509)—a table that holds all the alerts that will be activated on a Participant Device when a trigger has been activated.

A Researcher interfaces with the system via web pages served up by the Web Server (102) running the Web App (103). The Web App allows the Researcher to:

- Create a Data Request, for example, create Surveys, Triggers, Prompts or Annunciations. Triggers and Prompts allow a Researcher to initiate an interaction with a Participant, start or stop a software routine or request specific information recorded by the Participant Device.
- Enter Participant data
- Extract and view Participant Responses and context data related to Participant Responses or Items.

The Web App interfaces with the Server Database (107) to store data entered by the Researcher and to extract data for viewing or analysis by the Researcher. The Web App also will create transport files based on Researcher input to create a Data Request. The transport files (104) serve as a mechanism to easily transfer a Data Request to Participant Devices. This is described in more detail later.

Each Participant carries a Participant Device running a Participant Device App (109) provided by the Researcher. The Participant Device App interfaces with the Participant via a User Interface that can present Annunciations and Items setup by the Researcher. The Participant Device App creates a Participant Device Database (110), which may be a relational database, to store data collected by the Participant Device or entered Participant Responses and to store information about the Data Requests from the Researcher. The Participant Device App interfaces with the Server App (105) to download new Data Requests in the form of the transport files created by the Web App and to upload the data collected from the Participant Device or entered by the Participant to the Server Database.

The Web App, Server App, and Server Database may be located on a single Server or virtual Server or may be distributed across multiple Servers.

Detailed Description of Process Implementation

Create Data Request (201)

The web-based portion of the process has three major functions:

1. The creation of a Data Request via input from a web page (202)
2. Data Request data written to Server Database (203)
3. Creation of an transport file (204)

A Data Request is created by presenting a web page that prompts the Researcher to fill in data. The Web Application Data Request Form will have two main sections comprising a Trigger scheduler and a Survey designer.

Trigger Scheduler (FIG. 3)

A scheduled Trigger will result in the Participant Device App performing an action initiated by the occurrence of an event, the Trigger event. Through the Web App, a Researcher will be able to setup and configure one or multiple Triggers to be scheduled on one or multiple Participant Devices. The Trigger types can include but are not be limited to:

- time of day
- activity based on internal or external accelerometer data
- location based upon GPS position
- location based upon GPS position of friends
- answers to Survey questions The actions can include but are not limited to:

- prompt the Participant to take some action (such as view or respond to a Survey, take a picture and store the image, provide voice or text annotation for other data)
- record data from sensors associated with the Participant Device (such as location transceiver, accelerometer, gyroscope, light, temperature, or through local area communication)

The Triggers will have additional options that specify the details of how the Trigger will be executed (301). When the researcher completes the Trigger scheduling process, the data is written to the Server Database (203) via a php script and a transport file (204) (an XML example is displayed in the data transfer section below) is created by a php script that contains tags and attributes that describe the Metadata and the underlying data. The transport file is stored in a directory on the Server that is accessible to the Participant Device. An alternative to the creation of a file would be to create an formatted data stream instead of a file. This would eliminate the need to manage the deletion of files after the data is imported into the Participant Device database.

The Participant Device Application includes logic to monitor changes to the Server Database (107) SystemUpdates table and set a change flag when changes occur. The transport file is downloaded to the Participant Device and the new Trigger schedule is loaded into a local relational database (207).

Survey Designer (FIG. 4)

The Data Request Form also stores and retrieves data from the Server Database (107) that allows for the management of multiple Surveys. The Survey designer is a collection of files and database tables for managing Surveys that encompass a cycle of data and programming scripts to act on that data and display it and scripts that collect and store changes to the data and finally notify Participant Devices of the change. Surveys are prepared for deployment from tables in the Survey Database and may comprise:

- survey name
- id tag to uniquely identify itself
- Researcher
- Valid date/time ranges for Presentation
- Display characteristics (e.g., font or color)

Surveys are a collection of Items pointing to a single Survey in a parent-child relationship where the Survey is the parent and the Items are the children. The Question table contains the following columns:

- id tag to uniquely identify itself
- the text of the question
- type of question
- id of parent Survey All questions are assigned a question type and the list of valid question types is stored in a table called QuestionType (504). This table is linked to the Question table and all questions must contain a question type contained in the QuestionType table. The table contains the following columns:

- id to identify a question type
- description that further describes the question type The QuestionType table holds values that describe the type of Participant Response expected in answer to a question, these include:

Text

Single choice

Multiple choice

Date/time

Body weight or other numeric

Record voice or sound

Photo or image

When Participants are presented with questions with expected form of answers, including the single choice, multiple choice, text input, numeric input, image capture and voice record. For single choice responses the answers may be conveniently presented as radio buttons. Checkboxes are similarly convenient for multiple choice responses.

The data stored in the preceding tables needs to be displayed on a web page so the surveys can be created and modified. The first step for processing a Survey is to read the database with a programming script. Surveys are first presented to the Researcher as a list on a web page by calling a php script AjaxTest to retrieve a list of Surveys and present it on the web page.

From this point the Researcher will be able to manage Survey questions through controls on the Survey designer component of the Data Request Form (FIG. 4).

Managing survey questions is divided into five areas:

1. Adding questions. To add a question, the Researcher types the question into the question textbox (401). They will then choose the form of the question by clicking on the corresponding radio button (402). If the question is a single or multiple choice type question, the choice options can be created by clicking on the add question option and typing the option text into the text box that appears (403). If the Researcher decides this new option is not needed, it can be removed by selecting the remove option button. The process for saving the question and possible options is to first call an AJAX post function in javascript that collects the entered data and passes it to a php script. The php script will extract the data and load it into a local array. It will then write the data into the appropriate tables and return a status flag reflecting the success of failure of the operation.

2. Deleting questions. Existing questions can be deleted by clicking on a button placed next to all existing questions (404). The process for deleting a question is accomplished by calling and AJAX post function in javascript that passes the id of the question to a php script that runs an SQL query to delete the question which in turn deletes any options by using a foreign key command, cascade on delete.

3. Viewing existing options. Existing question options can be viewed by clicking on the options button next to it (405 & 406). The click event calls a javascript function that loads the options from the Server Database using Ajax programming techniques. Ajax is used for displaying options dynamically, and it will eliminate the need to refresh the entire page when only a small part of the Survey is being modified.

4. Ordering Questions. Questions can be reordered by clicking and dragging questions higher or lower until they are in the order desired. The reordering is implemented using Javascript and php sort functions. Survey design attributes such as background color or font can also be modified (407 and 408).

5. Branching. The Survey software is capable of branching to multiple questions based upon the answer the participant chooses. Questions have a branching attribute which points to a branching table that changes the order of the questions and ensures the Survey returns to correct subsequent Survey question. Branching in the Application would take the following steps.
   a) Researcher selects a question that would branch (701).
   b) Options of the branching questions would be assigned a destination question (702).
   c) Question set as a destination question would be tagged as a destination question (703).
   d) Logic in Application would ensure question tagged as destination question proceeds to the next question properly (704).

Commit Request Form Data to Database (203)

The data from the Request Form is written to the Server Database tables that have been designed along relational database rules. Writing the data to a Server Database instead of directly writing an XML file allows the data from the Request Form to be recalled and modified if needed. To save the Survey, the Researcher clicks the Submit button (409) and a javascript function called CreateXML collects data entered into the controls on the web page and passes them down to a php script called SurveySubmit.php. This php script commits all the data to the Survey, Question and QuestionOption tables.

Create Transport File (204)

The transport file is created by reading the Server Database and writing the data specified in the Request Form in XML format. A script called surveySubmit.php reads the Survey, Question and QuestionType tables and creates an XML file like the example below. The created XML files will be based upon the unique identifier that is assigned to each Participant Device. Another alternative to the creation of a file would be to create an XML data stream instead of a file. This would eliminate the need to manage the deletion of files after the data is imported into the Participant Device database.

Transfer Data (205)

The process to transfer the transport file from the Server to the Participant Device is initiated from the Participant Device. Each Participant Device has a unique identifier that is stored in a table with other useful details about the Participant Device that is sent to the Server App to identify which transport file to Download. The data transfer mechanism will be a network protocol initiated from the Participant Device that will pull the Survey transport file down from the Server (206). A table called SystemUpdates holds a list of all updates to system files like the Survey XML file. The Download process will use the HTTP protocol to Download the transport file. The transport file, based on XML, will contain Metadata inserted into XML attributes alongside the actual questions. Another alternative to initiate the Download of the transport file would be to use the Android Cloud to Device messaging system. This would involve registering the Web Server with Google and creating a series of messages concerning transport file creation. The Participant Device App would then be modified to monitor Android Broadcast messages from the Android operating system. The Participant Device App would receive a message whenever the Server Database SystemUpdates table changes and could then start the process to Download the Survey XML data.

Example of a Survey Transport Table Based on XML

```
<?XML version="1.0"?>
<root>
<Survey ID='1' SurveyName='Meals' color ='White'>
<Question ID='57' Question='Where did you eat dinner' QuestionOrder='1'>
<Option Question ID='57' OptionOrder='1' Description='at home'/>
<Option Question ID='57' OptionOrder='2' Description='at school'/>
<Option Question ID='57' OptionOrder='3' Description='at a restaurant'/>
</Question>
<Question ID='159' Question='How would you rate your weight' QuestionOrder='2'>
<Option QuestionID='159' OptionOrder='1' Description='1. Good'/>
<Option QuestionID='159' OptionOrder='2' Description='5. Too Heavy'/>
<Option QuestionID='159' OptionOrder='3' Description='10. Too light'/>
<Question>
<Question ID='161' Question='What meals did you have today?' QuestionOrder='3' >
<Option QuestionID='161' OptionOrder='1' Description='1. breakfast'/>
<Option QuestionID='161' OptionOrder='2' Description='2. lunch'/>
<Option QuestionID='161' OptionOrder='3' Description='3. dinner'/>
<Option QuestionID='161' OptionOrder='4' Description='4. at least one snack'/>
</Question>
<Question ID='160' Question='What is your awareness of fats in foods' QuestionOrder='4' >
<Option QuestionID='160' OptionOrder='1' Description='1. Not aware or it at all'/>
<Option QuestionID='160' OptionOrder='2' Description='2. Somewhat aware'/>
<Option QuestionID='160' OptionOrder='3' Description='3. Reasonably aware'/>
<Option QuestionID='160' OptionOrder='4' Description='4. Acutely aware'/>
<Question>
<Question ID='155' Question='Who are you with?' QuestionOrder='5' >
</Question>
</Survey>
</root>
```

The transport file will be downloaded every time the Participant Device App contacts the Server and determines updates have been made to the Triggers and Surveys assigned to that Participant Device. This file contains the instructions for the creation of Triggers and Prompts on the Participant Device.

Example of Transport Alert Manager File:

```
<root>
    <Items>
        <TPAItem ID='103' TriggerName='Test 4' TriggerType='3' SurveyID='5'/>
        <TPAItem ID='104' TriggerName='Post Meal 1' TriggerType='3' SurveyID='0'/>
        <TPAItem ID='105' TriggerName='Post Meal 2' TriggerType='3' SurveyID='2'/>
        <TPAItem ID='106' TriggerName='Test' TriggerType='2' SurveyID='1'/>
        <TPAItem ID='115' TriggerName='Random Morning' SurveyID='1'/>
        <TPAItem ID='116' TriggerName='Final 1' TriggerType='3' SurveyID='0'/>
    </Items>
    <Attributes>
        <Attribute_Trig_TimeBased Item ID = '103' Start = '09:00:00' End = '12:00:00'/>
        <Attribute_Trig_TimeBased Item ID = '104'Start = '00:00:00' End = '00:00:00'/>
        <Attribute_Trig_TimeBased Item ID = '105' Start = '00:00:00' End = '00:00:00'/>
        <Attribute_Trig_TimeBased Item ID = '106' TriggerTime = '06:30:00'/>
        <Attribute_Trig_TimeBased Item ID = '115' Start = '15:00:00' End = '18:00:00'/>
        <Attribute_Trig_TimeBased Item ID = '116' Start = '00:00:00' End = '00:00:00'/>
    </Attributes>
</root>
```

Collect Data (208)

Triggers:

The Trigger management logic of the Participant Device App has two components: Trigger Listeners and Trigger Handlers. When the transport file is downloaded, the information of the active Triggers and the corresponding actions are put into the Participant Device Database (207), and an Trigger configuration process is run. During the Trigger configuration process, active Triggers are registered with the Trigger Listeners. The role of the Trigger Listener is to detect or monitor for Trigger events and at that time send a message to the Trigger Handler that the event has transpired. An example of this is the location based trigger event, in which if a location based Trigger type has been registered, the Trigger Listener polls the location of the device periodically and compares to a registered location and radius. If the current location moves within the distance to the registered location, the Trigger Listener notifies the Trigger Handler that the location based event has transpired.

The Trigger Handler receives a notification that the Trigger event has occurred and through the Participant Device Database looks up what action should be taken based on the scheduled Triggers. The Trigger Handler then runs the logic to give the Annunciation and take the appropriate action. An example of this is the action notifying the Participant to take a Survey triggered by the location of the Participant Device (209).

Collection of Survey Data.

Figure 6:
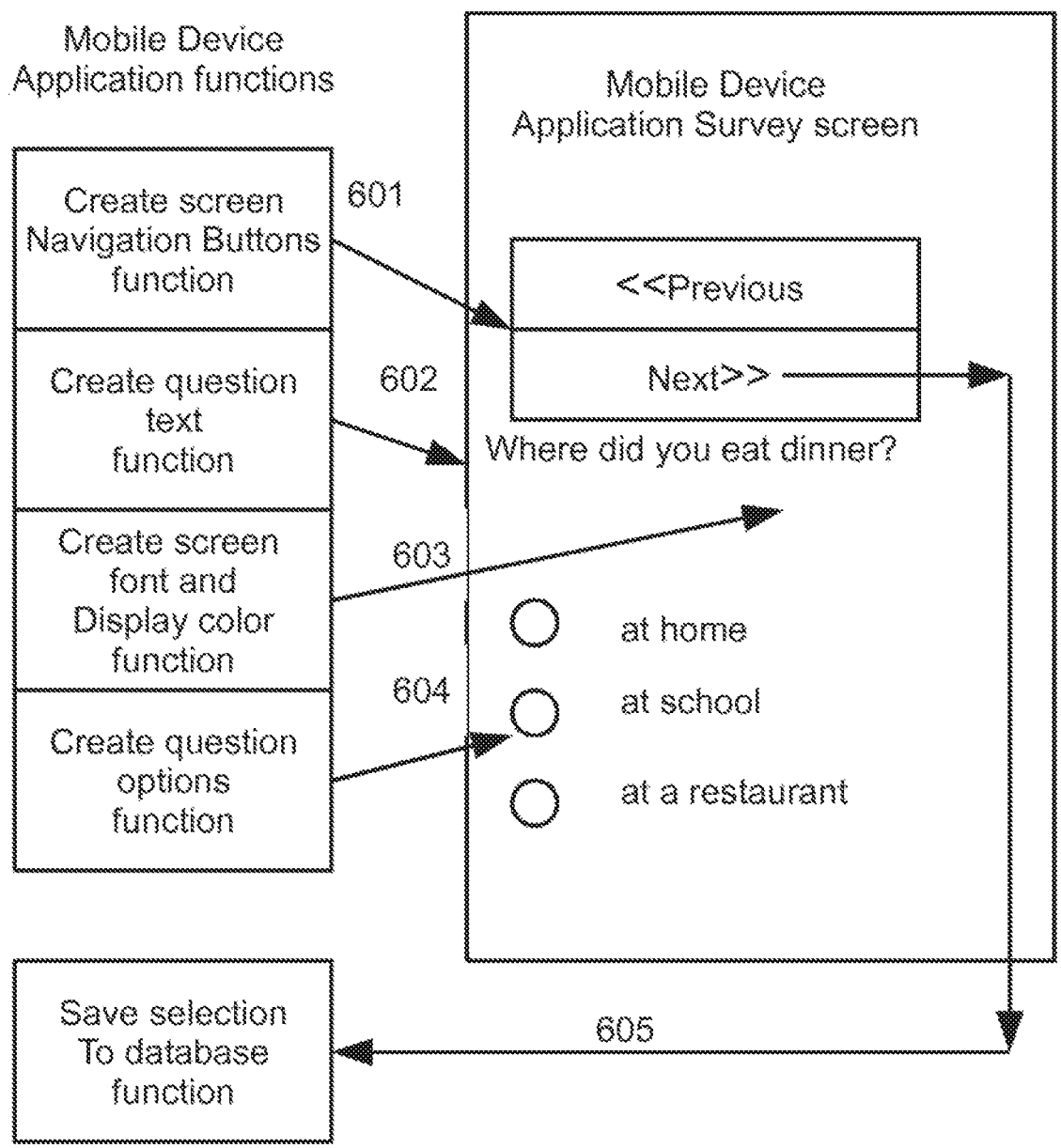
FIG. 6 is an example of a Survey presentation on a Participant Device.
Figure 7:
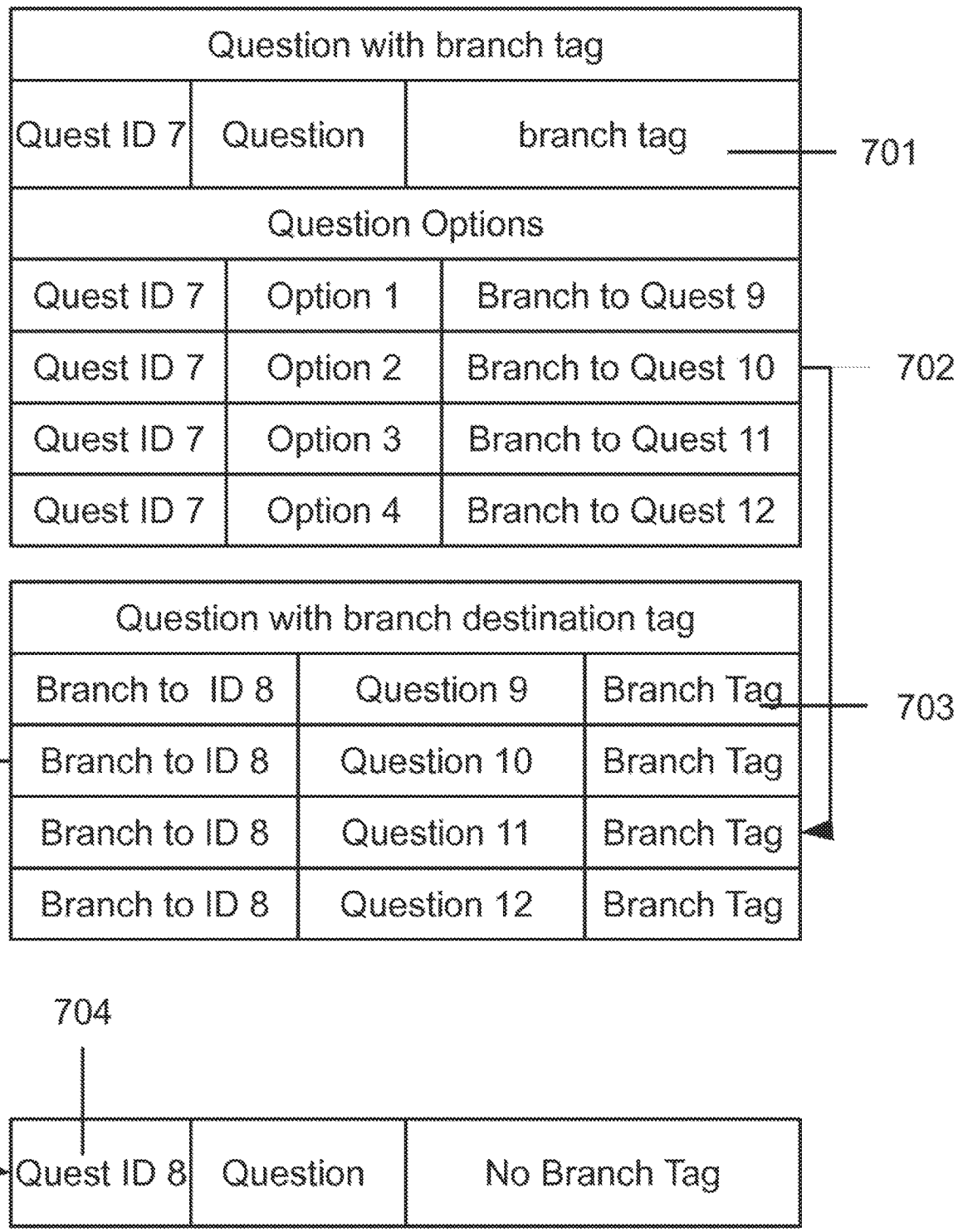
FIG. 7 is an example of a Survey question with the branching option.
Figure 8:
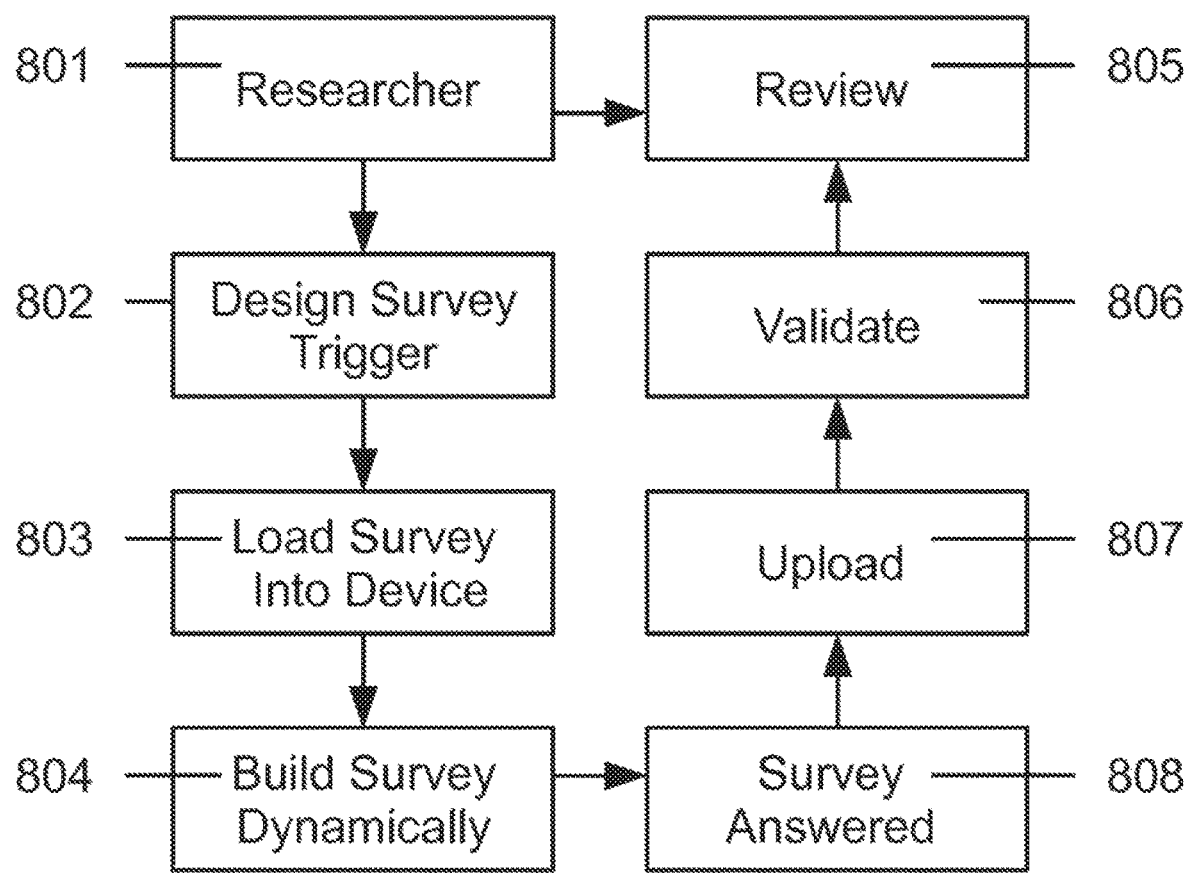
FIG. 8 is a summary view of the dynamic Survey/Trigger system.

The screen that displays the Survey questions is not a standard static screen that is normally displayed in Participant Devices. The Survey screen for the Mobile Application starts out as a blank screen. The typical Participant Device screen (a graphical User Interface screen) is based upon an XML file that is created before the Application is compiled and any change to the form requires a compiled Application. The concept of a graphical User Interface created by a developer during the design phase of an Application has the advantage of reduced complexity but this approach results in additional development time and cost when specifications change. With the dynamic Participant Device screen, a java function retrieves Metadata information from the Survey table in the Participant Device Database and creates the basic design of the screen (FIG. 6).

The background color, font and border factors are committed to the screen by reading the values taken from a Participant Device Database table. It then establishes variables as counters to track factors such as current question, current session, etc. Two buttons are displayed on the screen, named Previous and Next and activated in a prebuilt frameset as a first step in the building of the screen. These two buttons allow the Participant to navigate through the Survey (601). Basic screen setup factors such as fonts, colors and borders are set based on data read from the database (603). When this has been completed, the first question of the Survey is pulled from the database. The Survey question is then displayed (602) below the navigation buttons and the program then determines the type of question and a function appends an additional view based on the type of question. (604). There are currently five types of questions:

- Single choice questions displayed as a list of radio buttons. For single choice question, a series of radio button controls are created based on the question options and the options in turn are added to a radio group view and this radio group is appended to the screen. Each radio button has an OnClickListener event attached to it so the radio button will respond to the participant clicking the button.
- Multiple choice questions displayed as a list of check boxes. For multiple choice questions, a series of checkboxes are created based on the question options and each checkbox is added to a view. Each checkbox has an OnClickListener event attached to it so the checkbox will respond to the participant clicking the checkbox.
- Questions requiring text and displayed as a text box. The text question has an EditText control appended to the screen and the EditText control has an OnClickListener event attached to it.
- Date/time related questions displayed as a date time control. The Date/Time question has a TimePicker popup dialog control attached to it. This control sets it's date and time to the current date and time. Within the TimePicker control, an event function called onTimeSet captures the participant date/time selection.
- Questions requiring a voice recording. The voice recording screen is created by adding a record image button and a stop recording image button. The two buttons have a OnClickListener event attached and the click events will manage a MediaRecorder control.

All question items require an event that captures Participant interaction so the Application will know when an item has been selected. An individual listener event is assigned to each detail that will mark all selected items. With the question on the screen, the Application waits for the Participant to click the NEXT button (602). The selected values for the question are collected and written to a table in the Participant Device Database with the exception of voice recording. Voice recordings are saved as separate files with the name of the file describing the participant and date of recording (210). The participant can also choose the Previous button provided they are past the first question (601). The function that manages the previous button will remove any answers from the previous question and then load the appropriate question. When all of the Survey questions are answered, a function will group the answers as a unique event by the use of a session identifier, capture timestamps to measure Participant performance while answering questions then write the answers to the Answers table in the Participant Device database (605).

Transfer Data to Server Database (211)

The transfer of captured Participant Device data will involve pulling data out of the Participant Device Database and writing it to a file for transport. This process will be accomplished by using SQL (Structured Query Language) to create an output file. The naming of the file will help to identify the source. The filename will contain the user id and a date timestamp and a counter to give the file a unique identifier. The file can be comma delimited, straight text of a binary file, depending on how the Server App (105) is designed to process the file. The amount and type of data to transfer will be based upon settings in the Participant Device App. Once the file has been created, the Participant Device will invoke the Server App (105) to pull the file up and process it into the Database Server (106) using the HTTP post protocol.

An alternative method to uploading Participant Device data as a file is to read the Participant Device database and store the data in an array as key/pair values. The data is uploaded using the HTTP post protocol as each record is read from the database.

Validation of Data (212)

Uploaded data will be reviewed by the Server App to ensure it meets any validation requirements set on the Create Data Request Form (201). Data will also be validated by use of foreign keys on the tables that ensure data integrity. Any resulting errors will be captured, stored and then displayed on an exception web page.

Review/Analyze Data (213)

With the data loaded into the Database Server, the Server App will have functions that allow the Researcher a view into the uploaded data by means of reports and scripts. A web page will be created that displays the researcher name and institution. The page will have a calendar control so the researcher can view one or more days' worth of Survey answers. A list box will contain the names of the participants that have uploaded data. The answer data will be pulled from the answer table and joined with the question data and a timestamp through an SQL query. Further reports can be constructed as needed. The SQL query will be constructed in a php script that is called by the web page using AJAX programming techniques and will require a javascript function to populate the page.

Alternative Methods for Creating Surveys on Participant Devices

A Survey may be created for a Participant Device by using programming tools provided by the Participant Device's software development kit (SDK). The User Interface is designed in an integrated development environment and compiled into the Application when desired. Logic for displaying questions and saving answers is written specifically for the previously designed User Interface. Multiple surveys will require the creation of additional User Interfaces and logic to populate and retrieve data from them. The entire Application is compiled and loaded into the Participant Device. This method is effective but requires a programmer to create the User Interface and any ensuing changes.

Another method of using a Survey on a Participant Device is to use a Survey based upon a web page and running that web page from a browser contained in the Participant Device. This allows for an easily modified Survey but with the disadvantage of complete failure if there is no data connection.

PDA devices are capable of displaying and recording Survey information but typically do not have wireless connectivity. Surveys are designed on a personal computer with a custom Application that creates a Survey file. A Survey Application is loaded onto the PDA with the Survey file. The Survey Application reads the Survey file and the answers are copied off the PDA. Because most PDA do not have wireless connectivity, the PDA must be physically attached to the personal computer to copy the Survey file and the resulting answers.

We claim:

1. A data request system, comprising:
   a web server, running on a computer the web server configured for a researcher or other user to create multiple data tables for a study to be presented to individual participants being surveyed in a research study;
   a first data table, comprising a first data request including one or more data request items including:
   one or more questions, a request to take an action, or an instruction to record data from a sensor;
   a second table, comprising one or more trigger conditions to control the one or more data request items, the one or more trigger conditions including at least one of: (1) a time of day and an activity of the participant; or (2) a time of day and a location of the participant;
   a third table, designating individual participants participating in the study, and mobile personal computing devices personally associated with the individual participants being surveyed;
   a transport file, assembling at least the first and second tables, for download to a particular mobile personal computing device designated in the third table, such that an application installed on the particular mobile personal computing device downloads the transport file and configures the device to present to the participant one or more surveys, and obtain from the participant one or more responses to be stored, when the one or more trigger conditions specified in the second table are determined to have been met, the one or more trigger conditions including at least one of: (1) a time of day and an activity of the participant; or (2) a time of day and a location of the participant.

2. The system of claim 1, wherein the server is configured to gather one or more related questions or one or more requests into one or more titled surveys.

3. The system of claim 2, wherein the application is configured to present to the participant a list of two or more surveys that currently meet the one or more trigger conditions.

4. The system of claim 3, wherein the application is configured to remove a survey from the list when it no longer meets at least one trigger condition.

5. The system of claim 3, wherein the application is configured to remove a survey from the list within at least one of a specified ending date and time or duration.

6. The system of claim 3, wherein the application is configured to record at least one of a date or time when the participant selects a survey from the list.

7. The system of claim 1, wherein the application is configured to record at least one of the date or time at which a trigger condition was met.

8. The system of claim 1, wherein the application is configured to record the location of the particular mobile personal computing device when at least one trigger condition was met.

9. The system of claim 1, wherein the application is configured to record at least one of a date or time at which an item in the data request is started.

10. The system of claim 1, wherein the application is configured to record at least one of the date or time at which an item in the data request is completed.

11. The system of claim 1, wherein the participant device is configured to record at least one of a date or time at which an item in the data request is started.

12. A method of creating and administering data requests, the method comprising:
   creating one or more data tables on a web server, running on a computer, to hold information describing one or more of a data request, a participant, a participant device of a participant being surveyed in a research study, or return data;
   identifying one or more participants being surveyed and associating a participant device with an individual participant having access of that participant device;
   creating a data request comprising at least one item of a survey including one or more questions, a request to take an action, or data to be recorded from a sensor;
   configuring one or more triggers for each item in the data request to control the item on the participant device, the one or more triggers including at least one of: (1) a time of day and an activity of the participant; or (2) a time of day and a location of the participant;
   writing the data request and one or more triggers into a transport file for download to the participant device associated with the intended participant;
   downloading the transport file to the participant device with an application installed on the participant device;
   unpacking the transport file;
   registering the triggers on the participant device; and presenting to the participant one or more surveys, and obtaining from the participant one or more responses to be stored, in response to a determination that the one or more conditions specified by the trigger associated with that item have been met, the one or more triggers including at least one of: (1) a time of day and an activity of the participant; or (2) a time of day and a location of the participant.

13. The method of claim 12, further comprising gathering one or more related questions or requests into one or more named surveys.

14. The method of claim 13, further comprising removing one or more surveys from the list that no longer meet at least one trigger condition.

15. The method of claim 13, further comprising removing one or more surveys from the list within at least one of a specified beginning date or time or at least one of a specified ending date or time.

16. The method of claim 12, further comprising placing the two or more surveys that currently meet at least one trigger condition in a list presented to the participant in the application.

17. The method of claim 12, further comprising recording at least one of a date or time when a trigger condition was met.

18. The method of claim 12, further comprising recording the location of the participant device when a trigger condition is met.

19. The method of claim 12, further comprising recording at least one of a presentation date or time at which a question in the survey is presented to the participant and at least one of a completion date or time at which the participant completes a response to the presented item.

* * * * *